(12) United States Patent
Florent

(10) Patent No.: US 10,506,996 B2
(45) Date of Patent: Dec. 17, 2019

(54) MEDICAL IMAGING DEVICE WITH SEPARATE BUTTON FOR SELECTING CANDIDATE SEGMENTATION

(75) Inventor: Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 686 days.

(21) Appl. No.: 14/114,215

(22) PCT Filed: Apr. 17, 2012

(86) PCT No.: PCT/IB2012/051899
§ 371 (c)(1),
(2), (4) Date: Oct. 27, 2013

(87) PCT Pub. No.: WO2012/147006
PCT Pub. Date: Nov. 1, 2012

(65) Prior Publication Data
US 2014/0050304 A1    Feb. 20, 2014

(30) Foreign Application Priority Data
Apr. 28, 2011  (EP) ..................... 11305504

(51) Int. Cl.
G06F 3/048      (2013.01)
G06K 9/34       (2006.01)
A61B 6/00       (2006.01)
A61B 6/12       (2006.01)

(52) U.S. Cl.
CPC ............. *A61B 6/461* (2013.01); *A61B 6/467* (2013.01); *A61B 6/12* (2013.01); *A61B 6/463* (2013.01); *A61B 6/481* (2013.01); *A61B 6/504* (2013.01)

(58) Field of Classification Search
None
See application file for complete search history.

(56) References Cited

U.S. PATENT DOCUMENTS 5,353,354 A  * 10/1994 Keller ..................... A61B 8/14
                                              382/128
7,620,234 B2   11/2009 Taylor
7,783,094 B2    8/2010 Collins et al.
(Continued)

FOREIGN PATENT DOCUMENTS

JP    2000010987 A    1/2000
JP    2001238873 A    9/2001
(Continued)

*Primary Examiner* — Patricia J Park

(57) ABSTRACT

A medical imaging device allowing easy and robust representation of anatomic structures within a region of interest in a patient body includes an image acquisition device, an image segmentation device, a visualization device and a separate selection button. In an image of the region of interest, anatomic structures may be automatically identified using image segmentation techniques. Therein, not only one but a plurality of candidate images including differently identified anatomic structures is provided. The plurality of candidate images may be visualized on a display sequentially or in an overlying manner. Using the easy accessible and easy to handle separate selection button, a physician may cycle through the plurality of candidate images and manually select one candidate image only by activating the selection button for further exploitation.

20 Claims, 2 Drawing Sheets

(56) References Cited

U.S. PATENT DOCUMENTS

| | | | | |
|---|---|---|---|---|
| 8,547,402 B2* | 10/2013 | Kreeger | ............. | G06F 19/3406 345/629 |
| 2002/0008765 A1* | 1/2002 | Ejima | ................ | H04N 5/23293 348/239 |
| 2006/0025671 A1 | 2/2006 | Kusunoki | | |
| 2006/0052684 A1* | 3/2006 | Takahashi | ........... | G06F 19/3406 600/407 |
| 2006/0071947 A1* | 4/2006 | Ubillos | ................. | G06F 3/0481 345/648 |
| 2007/0173717 A1* | 7/2007 | Camus | ................. | A61B 8/4416 600/427 |
| 2008/0159708 A1* | 7/2008 | Kazama | ................... | H04N 5/91 386/333 |
| 2009/0175407 A1* | 7/2009 | Harer | ...................... | A61B 6/032 378/20 |
| 2009/0195514 A1* | 8/2009 | Glynn | ...................... | A61B 8/12 345/173 |
| 2009/0279767 A1* | 11/2009 | Kukuk | ................. | G06T 7/0044 382/132 |
| 2009/0305204 A1* | 12/2009 | Connolly | ................. | G09B 7/02 434/219 |
| 2010/0185211 A1* | 7/2010 | Herman | ................. | B25J 9/1065 606/130 |
| 2011/0026786 A1 | 2/2011 | Mohamed | | |
| 2011/0200251 A1* | 8/2011 | Chin | .................... | G06K 9/4642 382/168 |
| 2012/0176408 A1* | 7/2012 | Moriya | ................ | A61B 5/0013 345/629 |

FOREIGN PATENT DOCUMENTS

| | | |
|---|---|---|
| JP | 2007175434 | 7/2007 |
| JP | 2009291313 A | 12/2009 |
| WO | WO2003045244 | 6/2003 |
| WO | WO2005114575 | 12/2005 |
| WO | WO2006109269 | 10/2006 |
| WO | 2011044295 A2 | 4/2011 |
| WO | WO2011039681 | 4/2011 |

* cited by examiner

MEDICAL IMAGING DEVICE WITH SEPARATE BUTTON FOR SELECTING CANDIDATE SEGMENTATION

CROSS-REFERENCE TO PRIOR APPLICATIONS

This application is the U.S. National Phase application under 35 U.S.C. § 371 of International Application Serial No. PCT/IB2012/051899, filed on Apr. 17, 2012, which claims the benefit of European Application Serial No. 11305504.0, filed on Apr. 28, 2011. These applications are hereby incorporated by reference herein.

FIELD OF THE INVENTION

The present invention relates to a medical imaging device adapted for user-friendly representation of anatomic structures in an image of a region of interest in a patient body.

BACKGROUND OF THE INVENTION

In medical interventions such as invasive or minimally invasive interventions it may be necessary to visualize anatomic structures within a region of interest in a patient body to a physician. Based on such visualized anatomic structures, the physician can then plan or perform the medical intervention including e.g. treating diseased tissue in the anatomic structure or introducing a medical device to a specific position within the anatomic structure.

As an example, in X-ray guided vascular interventions it may be important to get outlines of specific vessels to guide percutaneous devices to a targeted lesion. For instance, in a percutaneous treatment of an abdominal aortic aneurysm, a stent graft should be placed below the renal arteries, so as to avoid blocking those arteries and impairing the kidneys. A proper visualizing and outlining of those arteries as they emerge from the aorta may help in accurately placing of the device.

Conventionally, different approaches for visualizing and outlining anatomic structures in an image of an anatomical region of interest have been proposed. For example, vessel outlining may be manually drawn by a vascular surgeon. However, this is typically a tedious solution in a medical intervention environment where interaction by a physician is to be held at a minimum.

Another approach consists in automatically detecting a vessel anatomy structure in a previously acquired angiogram, i.e. an X-ray image acquired while contrast medium being present in the vessels, by automatically identifying or selecting the vessels of interest and finally super-imposing selected vessel outlines to fluoroscopy images acquired during the actual medical intervention in order to allow precise placement of a medical device.

For example, WO 2005/114575 A1 describes an image processing system for automatic segmentation of a 3D tree-like tubular surface of an object.

However, while automatic image-based segmentation techniques may reduce or avoid any necessary interactions of a physician for providing a visual representation of anatomic structures, it has been observed that such automatic image-based segmentation is rarely perfect. Accordingly, particularly in medical interventions where the visualization of anatomic structures is a key factor for the success of the intervention, automatic image-based segmentation techniques do often not provide a sufficient degree of reliability.

SUMMARY OF THE INVENTION

There may be a need for a medical imaging device allowing a visualization of anatomic structures in a region of interest of a patient body with high reliability while at the same time requiring a minimum of user interaction.

Such need may be met with the medical imaging device according to the independent claim. Embodiments of the invention are described in the dependent claims.

According to an aspect of the present invention, a medical imaging device comprising an image acquisition device, an image segmentation device, a visualization device and a separate selection button is proposed. Therein, the image acquisition device is adapted for acquiring an image of a region of interest in a patient body. The image segmentation device is adapted to automatically identify anatomic structures or device structures within an acquired image using image segmentation techniques. Furthermore, the image segmentation device is adapted to provide a plurality of candidate images comprising differently identified anatomic structures. The visualization device is adapted to visualize the plurality of candidate images on a display. The selection button is provided and arranged such that the imaging device is adapted for manually selecting one candidate image out of the plurality of candidate images only by activating the selection button.

According to embodiments of the invention the medical imaging device, on the one hand, is adapted for automatically identifying anatomic structures using segmentation techniques and, on the other hand, does not completely rely on the automated segmentation techniques but allows for a minimum user interaction in order to increase the robustness of the correct representation of the anatomic structures. Therein, the image segmentation device is adapted to not only provide a single image including an automatically identified anatomic structure but to provide a plurality of candidate images in which each candidate image represents an identified anatomic structure which has been identified using different image segmentation results. Therein, a probability that one of these candidate images correctly identifies and represents the anatomic structures comprised in the region of interest is very high. The medical imaging device then includes a separate selection button which may be used by a physician to manually select one candidate image out of the plurality of candidate images which candidate image, based e.g. on the physician's experience, has the highest probability of correctly identifying the anatomic structures. Therein, as during a medical intervention a physician may hardly concentrate on handling any complicated devices, the selection button should be provided and arranged in a way such that the physician may easily activate this button during a medical intervention.

These and other features and possible advantages of the present invention will become apparent from and elucidated with reference to embodiments described hereinafter.

BRIEF DESCRIPTION OF THE DRAWINGS

Exemplary embodiments of the invention will be described in the following with reference to the attached drawings wherein the description and drawings shall not limit the scope of the invention.

The figures are only schematical and not to scale.

DETAILED DESCRIPTION OF EMBODIMENTS

Figure 1:
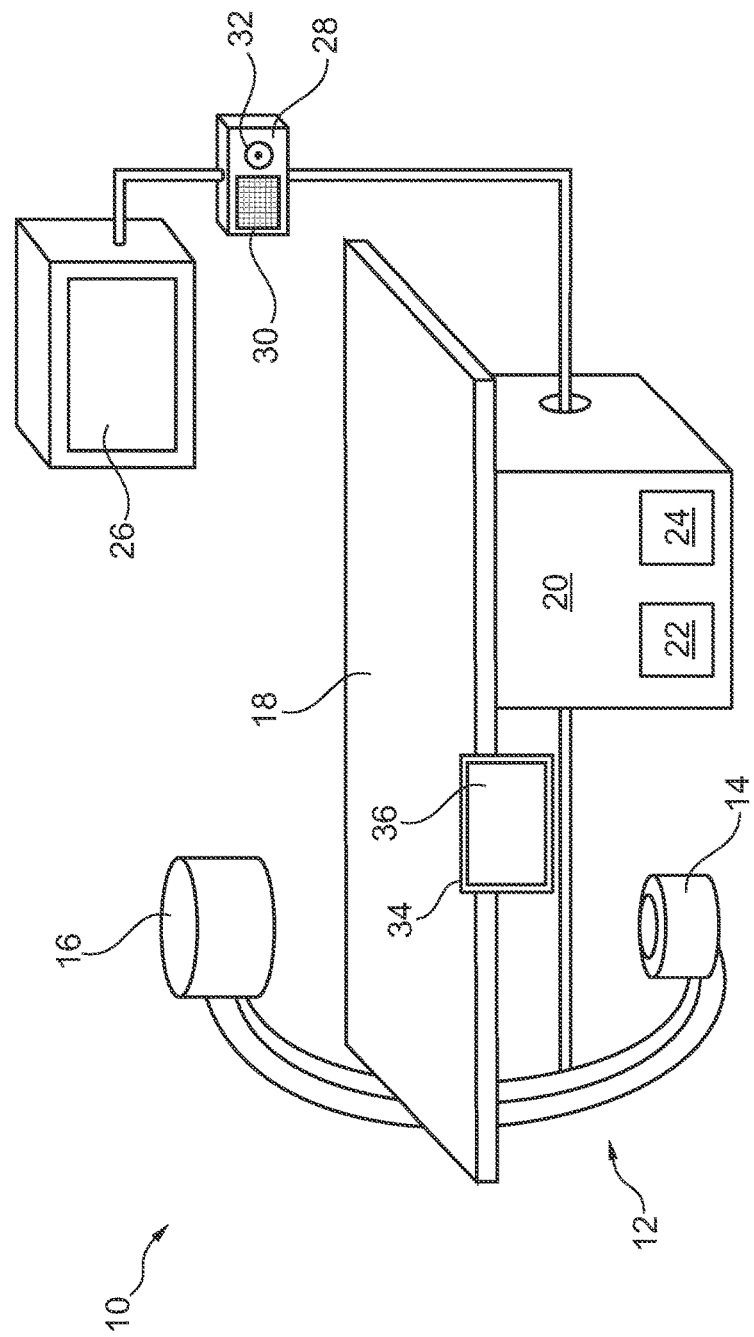
FIG. 1 shows a medical X-ray imaging device according to an embodiment of the present invention.

FIG. 1 schematically shows an X-ray medical imaging device 10 according to an embodiment of the present invention.

The imaging device 10 comprises an image acquisition device 12 in the form of a C-arm X-ray image acquisition device comprising an X-ray source 14 and an opposing X-ray detector 16. The C-arm X-ray imaging device 12 is positioned at a patient table 18 such that X-radiation emitted by the X-ray source 14 may be transmitted through a region of interest in a patient body lying on the patient table 18 before being detected by the X-ray detector 16.

Image information acquired by the X-ray detector 16 may then be transmitted to a computing device 20 arranged e.g. underneath the patient table 18. The computing device comprises an image segmentation device 22 and a visualization device 24 as schematically indicated in FIG. 1. These segmentation device and visualization device 24 may be implemented as separate electronic circuits, as shown, or may be combined in one single circuit.

The segmentation device 22 is adapted to perform image segmentation techniques in order to automatically identify anatomic structures or device structures, i.e. generally potentially relevant structures, within an image acquired by the X-ray detector 16 of the image acquiring device 12. Using these image segmentation techniques with e.g. different starting conditions or boundary conditions may result in identifying anatomic structures within the region of interest in different ways. Accordingly, the image segmentation device may provide a plurality of candidate images in which the anatomic structures or device structures are differently identified, respectively.

The term "candidate images" may refer to any representation which may visualize a quantitative and/or qualitative feature relating to the anatomic structures or device structures to be identified. For example, the candidate images may visualize a contour of the anatomic structures or device structures. Alternatively, the candidate images may encompass a quantitative representation such as a volume-flow value list among which the doctor could choose a right value.

The visualization device 24 is adapted to visualize candidate images on a display 26. The display 26 may be provided as a touch screen such that it may be used by a user to input further information data to the computing device 20. Additionally, a separate input device 28 comprising a keyboard 30 and a trackball 32 or mouse is provided for inputting data to the computing device 20.

As the image segmentation device 22 may provide a plurality of candidate images comprising differently identified anatomic structures in the region of interest of the patient body, a physician or interventionalist shall be enabled to select one specific candidate image out of the plurality of candidate images as being most probable a correct representation of the anatomic structures.

For this purpose, a selection button 34 is provided. The selection button 34 is located at the patient table 18 such that it may easily be activated by the physician during the medical intervention in which the physician has to stay close to the patient lying on the table 18. In other words, while the entire medical imaging device 10 comprises other input devices such as the touch screen 26 or the input device 28 for inputting data to the computing device 20, these input devices are supplemented by an additional separate selection button 34 which is also connected to the computing device 20 and which, due to its positioning being spatially separate to the display 26 and the input device 28 and being arranged at or close to the patient table, may be easily handled during a medical intervention by the intervening physician.

Furthermore, the selection button 34 may have a size such that an activation surface 36 of the selection button 34 is sufficiently large to be pressed not only with fingers but also for example by a physician's elbow or other body part. For example, an activation surface 36 of the selection button 34 may have more than 5 cm$^2$ and preferably more than 25 cm$^2$. It may feature a rounded protruding shape, making it particularly fit to easy access while limiting unintended collisions. It may also feature a smooth rounded and groove-less surface adapted to sterile environment where the accumulation of dust or organic particles should be avoided.

The selection button 34 may be realized as a toggling button, a switch button, or any other kind of button allowing easy handling and providing a signal to the computing device 20 upon activation of the button 34. The button may be a general purpose, context-sensitive toggling device which may be easy to reach and to activate even without looking at it. It may be "general purpose" in that it may be used also for different tasks. Furthermore, it may be "context-sensitive" in that, additionally to its main purpose of allowing selection of a candidate image as described in further detail below, it can also be used to cycle through different objects or choices.

Figure 2:
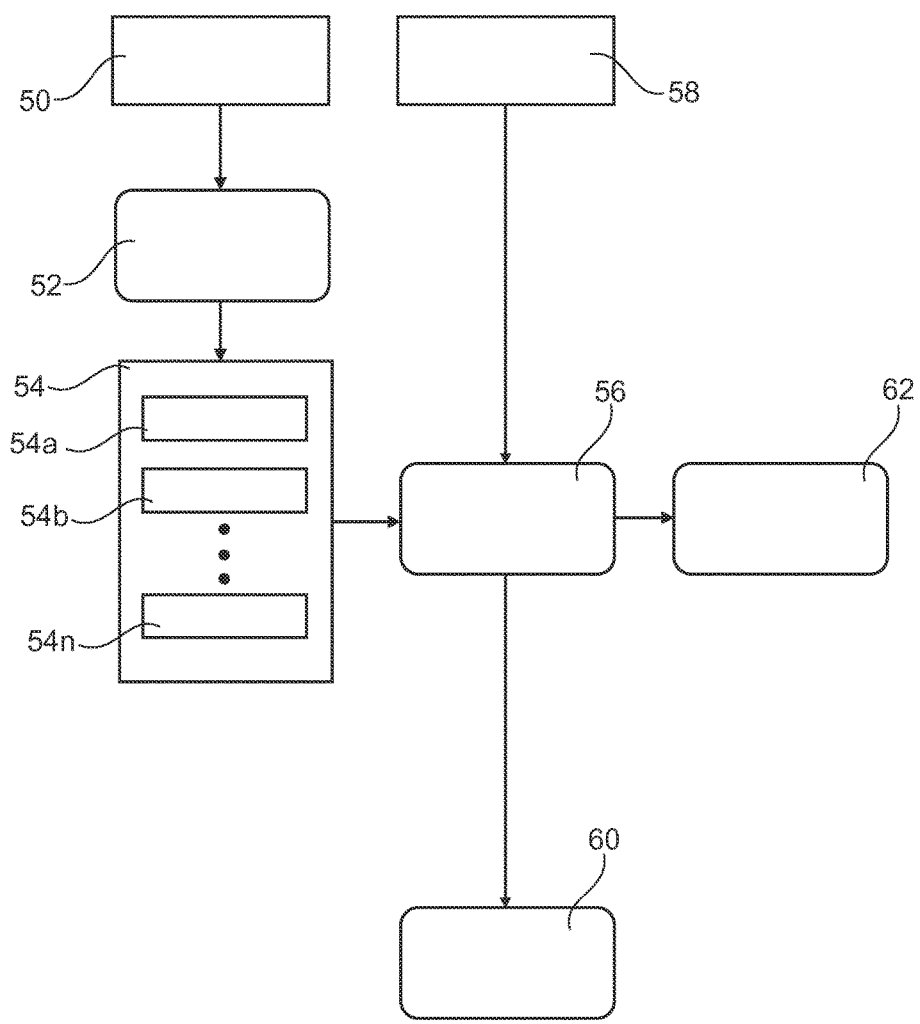
FIG. 2 shows a diagram representing an operation mode of a medical imaging device according to an embodiment of the present invention.

Embodiments of modes of operation of the medical imaging device 10 will now be further explained with reference to the diagram shown in FIG. 2.

Generally, input data 50 representing an image acquired by the image acquisition device may be any data being compatible with pseudo-automatic segmentation techniques such as e.g. vessel outlining. As further examples, a variety of input data concerning interventions or planning phases may also be considered. In particular, the dimension of input data 50 is not specified or limited. For instance, input data may be 2D (plain image), 2D+time (image series), 3D (volume), 3D+time (volume series), functional data including flow or velocity measurements, diffusion tensor images, etc.

The input data are then provided to a segmentation process 52. Such segmentation process 52 may be very general and may comprise various segmentation techniques, starting conditions and/or boundary conditions as long as it produces a limited set 54 of possible candidate images 54a, 54b, . . . , 54n comprising alternative representations of anatomic structures or device structures within a region of interest. The anatomical structures are not specified and might be any organic structure, for instance vascular structures, bone structures, soft tissue structures, pathologic elements, etc. Likewise, the device structures are not specified and might be any elements that do not originate from the patient but which are nonetheless of interest during the considered intervention. This includes interventional tools such as catheters, guide-wires, introducers, delivery devices, but it also includes also sort of prostheses or endo-prostheses such as stents, flow diverters, artificial valves, grafts, sternal wires, staples, pace-makers, etc.

One common feature to all these organic or non-organic structures is that they can somehow be represented on a screen. This representation might be indirect or approximate. For instance a vessel section might be represented as a simple tubular structure made of a centreline and of a set of elliptical cross-sections, or a tumour might be simply represented by its contours. But, while this screen representation may be schematic or approximate, it should provide enough information to allow the intervention staff to be able to designate the structure or structures of interest.

The computing device 20 or particularly the visualization device 24 comprised therein may provide a ranking list indicating a relevance factor for each candidate image 54a, . . . , 54n. The relevance factor may for example indicate a confidence with which the candidate image is believed to provide a correct identification of the anatomic structures of interest. Alternatively, the relevance factor could also refer to several potentially interesting anatomic structures from which a physician may then select one specific anatomic structure of current interest.

In a subsequent procedure, one specific candidate image shall be selected 56 from the multiplicity of candidate images 54a, . . . , 54n for further exploitation 60 of such most promising candidate image and/or displaying 62 such candidate image on the display 26. Different possible selection modes will be presented herein subsequently.

For example, the visualization device 24 may visualize one single specific candidate image at a time. The visualization device may start with a default one of the candidate images 54a, . . . , n and then, upon activating 58 the selection button 34 by a user, visualize a next candidate image. Therein, the currently visualized candidate image shall be the currently selected candidate image, i.e. upon activating the selection button 34 a next candidate image may be visualized and selected.

Alternatively, the visualization device 24 may automatically and consecutively visualize the plurality of candidate images individually, i.e. in a sequence, wherein each candidate image is visualized for a preset time period of e.g. 1 s to 10 s, similar to a slide show. Upon activation of the selection button 34, the sequential representation, i.e. the slide show, is stopped and the currently visualized candidate image is selected for subsequent exploitation.

As a further alternative, the visualization device 24 may represent all of the plurality of candidate images 54a, . . . , 54n simultaneously in an overlying manner. Therein, one specific candidate image may be visualized in an emphasized manner using for example highlighting, different colours, symbols, etc. Upon activating the selection button, a next candidate image is visually emphasized and thereby selected for subsequent exploitation.

Alternatively, the visualization device 24 may automatically cycle from one candidate image to a next candidate image in a sequence, each candidate image being visually emphasized for a preset time period. A user may stop such "overlying slide show" by activating the selection button thereby selecting the specific candidate image currently visually emphasized for subsequent exploitation.

The sequential separate visualization of single candidate images or alternatively the sequential visual emphasizing in a superposition of all or a plurality of candidate images may be performed in an order of the ranking list determined previously and indicating relevance factors for each candidate image. For example, a visual representation or a visual emphasizing of a candidate image having the highest relevance factor may be used at the beginning of the selection procedure.

The visualization device may then sequentially visualize a series of all candidate images and, after visualizing a last candidate image of the series, cycle back for visualizing the first image of the series. In other words, every time the selection button 34 is activated by "toggling", the visualization device continues cycling ahead through the candidate list. At the end of the candidate list, the visualization device jumps back to the beginning of the candidate list.

Therein, the visualization device may indicate to a user that the entire series of candidate images has been visualized or visually emphasized, i.e. one full visualization cycle has been completed.

The candidate image selected for further exploitation may be used for different purposes.

In one specific embodiment, the image acquisition device 12 is an X-ray image acquisition device which is adapted for acquiring an angiogram image of the region of interest. In other words, the X-ray image acquisition device may acquire an image of the region of interest while contrast medium is present within the region of interest. From such angiogram image, the segmentation device may provide a plurality of candidate images. These candidate images may be stored for subsequent use. During a subsequent medical intervention, the visualization device may superimpose one or more of the stored candidate images on a fluoroscopy image (i.e. without contrast agent) of the same region of interest acquired during the medical intervention. Using the selection button 34, the physician may then, during the medical intervention, select one of the plurality of candidate images which best matches the fluoroscopy image. A representation of the anatomic structures in the region of interest according to such candidate image may then be visualized on the display 26, possibly overlaying the current fluoroscopy image.

Due to the easy access and easy handling of the separate selection button 34, the physician may easily cycle through and evaluate each of a plurality of candidate images which have been previously determined using automatic image segmentation techniques. Thereby, while a plurality of candidate images may be provided using automated segmentation of acquired images of a region of interest, the physician gets an easy option to improve the robustness of the correct representation of anatomic structures within the region of interest by using his personal experience in selecting a most promising one of the candidate images for further exploitation.

In the claims, the word "comprising" does not exclude other elements or steps, and the indefinite article "a" or "an" does not exclude a plurality. A single processor or other unit may fulfill the functions of several items cited in the claims. The mere fact that certain measures are cited in mutually different dependent claims does not indicate that a combination of these measures cannot be used to advantage.

LIST OF REFERENCE SIGNS

10 Medical imaging device
12 Image acquisition device
14 X-ray source
16 X-ray detector
18 Patient table
20 Computing device
22 Image segmentation device
24 Visualization device
26 Display
28 Input device
30 Keyboard
32 Trackball
34 Selection button
36 Activation surface
50 Input data
52 Segmentation
54 List of candidate images
56 Selection 58 Button activation
60 Exploitation
62 Displaying

The invention claimed is:

1. A medical imaging device comprising:
an image acquisition device configured to acquire an image of a region of interest in a patient body;
an image segmentation device configured to automatically identify anatomic or device structures within an acquired image using image segmentation techniques, wherein the image segmentation device is further configured to provide a plurality of candidate images representing differently identified anatomic or device structures;
a visualization device configured to visualize the plurality of candidate images on a display; and
a separate user interface consisting of a separate selection button,
wherein the imaging device is configured for manual selection of one candidate image out of the plurality of candidate images only by activating the selection button,
wherein the separate user interface consisting of the selection button is spatially separate from the display and is provided in addition to and separate from other input devices configured for inputting data to a computing device and is also connected to the computing device, and
wherein the separate user interface consisting of the selection button is located at a patient table configured to support the patient body for being easily handled during a medical intervention by an intervening physician.

2. The medical imaging device of claim 1, wherein the visualization device is configured to visualize one specific candidate image at a time and, upon activating the selection button, to visualize and select a next candidate image.

3. The medical imaging device of claim 1, wherein the visualization device is configured to visualize the plurality of candidate images simultaneously in an overlying manner and to visually emphasize one specific candidate image at a time and, upon activating the selection button, to visually emphasize and select a next candidate image.

4. The medical imaging device of claim 1, wherein the visualization device is configured to visualize the plurality of candidate images individually in a sequence, each candidate image being visualized for a time period, and a specific candidate image being selected by activation of the selection button while this candidate image being visualized.

5. The medical imaging device of claim 1, wherein the visualization device is configured to visualize the plurality of candidate images simultaneously in an overlying manner and to visually emphasize the plurality of candidate images individually in a sequence, each candidate image being visually emphasized for a time period, and a specific candidate image being selected by activation of the selection button while this candidate image being visually emphasized.

6. The medical imaging device of claim 1, wherein the segmentation device is configured to provide a ranking list indicating a relevance factor for each candidate image.

7. The medical imaging device of claim 6, wherein the visualization device is configured to visualize the candidate images in an order of the ranking list.

8. The medical imaging device of claim 1, wherein the visualization device is configured to sequentially visualize a series of all candidate images and to, after visualizing a last candidate image of the series, cycle back for visualizing a first image of the series.

9. The medical imaging device of claim 8, wherein the visualization device is configured to indicate to a user that an entirety of the series of candidate images has been visualized.

10. The medical imaging device of claim 1, wherein the image acquisition device is configured to acquire an angiogram image of the region of interest and wherein the segmentation device is configured to provide a plurality of candidate images comprising differently identified anatomic structures based on the angiogram image and store the plurality of candidate images and wherein the visualization device is configured to superimpose the candidate images on a fluoroscopy image of the same region of interest subsequently acquired during a medical intervention.

11. The medical imaging device of claim 1, wherein the image acquisition device comprises an X-ray image acquisition device.

12. A medical imaging device comprising:
an imager having a detector configured to acquire an image of a region of interest in a patient body;
a processor configured to automatically identify anatomic or device structures within an acquired image using image segmentation techniques, wherein the processor is further configured to provide a plurality of candidate images representing differently identified anatomic or device structures;
a display configured to display the plurality of candidate images; and
a user interface consisting of a selection button configured to be manually activated for manual selection of one candidate image out of the plurality of candidate images only by activating the selection button,
wherein the user interface consisting of the selection button is spatially separate from the display and is provided in addition to and separate from other input devices configured to input data to the processor and is also connected to the processor, and
wherein the selection button is located a patient table configured to support the patient body for being easily handled during a medical intervention by an intervening physician for the manual selection.

13. The medical imaging device of claim 12, wherein the display is configured to display one specific candidate image at a time and, upon activating the selection button, to display and select a next candidate image.

14. The medical imaging device of claim 12, wherein the display is configured to display the plurality of candidate images simultaneously in an overlying manner and to visually emphasize one specific candidate image at a time and, upon activating the selection button, to emphasize and select a next candidate image.

15. The medical imaging device of claim 12, wherein the display is configured to display the plurality of candidate images individually in a sequence, each candidate image being displayed for a time period, and a specific candidate image being selected by activation of the selection button while this candidate image being displayed.

16. The medical imaging device of claim 12, wherein the display is configured to display the plurality of candidate images simultaneously in an overlying manner and to visually emphasize the plurality of candidate images individually in a sequence, each candidate image being visually emphasized for a time period, and a specific candidate image being selected by activation of the selection button while this candidate image being visually emphasized.

17. The medical imaging device of claim 12, wherein the processor is configured to provide a ranking list indicating a relevance factor for each candidate image, and wherein the display is configured to display the candidate images in an order of the ranking list.

18. The medical imaging device of claim 12, wherein the display is configured to sequentially display a series of all candidate images of the plurality of candidate images and to, after displaying a last candidate image of the series, cycle back for visualizing a first image of the series.

19. The medical imaging device of claim 18, wherein the display is configured to display an indication that an entirety of the series of candidate images has been displayed.

20. The medical imaging device of claim 1, wherein the selection button includes an activation surface having a size configured to be pressed by an elbow of the intervening physician, the activation surface having a rounded protruding shape to limit unintended activation.

\* \* \* \* \*